United States Patent [19]

Harris et al.

[11] 4,150,065

[45] Apr. 17, 1979

[54] OLEFIN ISOMERIZATION USING ALKALI METAL-GRAPHITE INTERCALATE CATALYST

[75] Inventors: Jesse R. Harris; Marvin M. Johnson, both of Bartlesville, Okla.

[73] Assignee: Phillips Petroleum Company, Bartlesville, Okla.

[21] Appl. No.: 817,765

[22] Filed: Jul. 21, 1977

[51] Int. Cl.$^2$ ............................................. C07C 5/24
[52] U.S. Cl. ................................................ 260/683.2
[58] Field of Search ...................................... 260/683.2

[56] References Cited

U.S. PATENT DOCUMENTS

| 2,965,689 | 12/1960 | Roebuck et al. | 260/683.2 |
| 2,994,727 | 8/1961 | Appell et al. | 260/683.2 |
| 3,176,048 | 3/1965 | Yeo et al. | 260/683.2 |

Primary Examiner—Veronica O'Keefe

[57] ABSTRACT

A method for shifting the double bond in an aliphatic 1-olefin containing more than three carbon atoms in which the 1-olefin is contacted with a catalyst comprising an alkali metal selected from potassium, rubidium, and cesium intercalated in a graphite or graphitized carbon black.

8 Claims, No Drawings

OLEFIN ISOMERIZATION USING ALKALI METAL-GRAPHITE INTERCALATE CATALYST

BACKGROUND OF THE INVENTION

This invention relates to isomerization of aliphatic 1-olefins. In one of its aspects this invention relates to alkali metal-graphite intercalate catalysts.

Isomerization of 1-olefins using a potassium catalyst is known in the art. At relatively low temperature, about 25° C., this isomerization gives a trans/cis mole ratio of ½, but at higher temperatures in the range of 100° C. or higher this selectivity is not present so that the trans/cis mole ratio is about 1. It has now been discovered that certain alkali metal-graphite intercalates can be used in a range of temperatures extending well above 100° C. to yield a low trans/cis mole ratio of isomerized product from aliphatic 1-olefin feedstock.

It is, therefore, an object of this invention to provide a method for isomerizing aliphatic 1-olefin. It is another object of this invention to provide an isomerization catalyst which yields isomerized products from aliphatic 1-olefin maintaining low trans/cis ratios of the internal olefins formed at moderately elevated temperature.

Other aspects, objects, and the various advantages of this invention will become apparent upon reading the specification and the appended claims.

STATEMENT OF THE INVENTION

According to this invention, a method is provided for shifting the double bond in an aliphatic 1-olefin containing more than three carbon atoms to a more centrally located portion by contact with an alkali metal-graphite intercalate catalyst. The catalysts are effective in maintaining low trans/cis ratios of the internal olefins formed in a range of temperature from about ambient through temperatures that are moderately elevated.

Suitable feeds for the process include 1-olefins containing from 4 to about 20 carbon atoms per molecule or even more. A limiting factor in selection of 1-olefin feedstock is that the products formed from them must contain cis and trans isomers. Thus, each of the carbon atoms forming the double bond in the 1-olefin must originally contain at least 1 hydrogen atom. A generic formula is shown below:

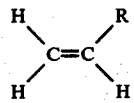

R is selected from alkyl groups containing from 2 to about 13 carbon atoms. Examples of suitable 1-olefins are: 1-butene, 1-pentene, 1-hexene, 1-heptene, 1-octene, 1-nonene, 1-decene, 1-undecene, 1-dodecene, 1-tridecene, 1-tetradecene, 1-pentadecene, and the like, 4-methyl-1-pentene, 4-methyl-1-hexene, 5-methyl-1-hexene, 4-methyl-1-heptene, 5-methyl-1-heptene, 6-methyl-1-heptene, 4-methyl-1-octene, 5-methyl-1-octene, 6-methyl-1-octene, 7-methyl-1-octene, and the like. A presently preferred 1-olefin is 1-butene and high selectivity to cis-2-butene is maintained over the reaction temperature range utilized.

Reaction conditions suitable in the process are not critical and can vary appreciably, but will usually fall in a range as follows: Reaction temperature can range from about 25° to about 300° C., preferably from about 25° to about 150° C. Reaction pressure can vary from about 0.5 to about 50 atmospheres (0.05–5 MPa), preferably from about 0.5 to about 5 atmospheres (0.05–0.5 MPa). Weight hourly space velocity (WHSV) of the feed can range from about 0.02 to about 20, preferably from about 0.04 to about 10.

Catalysts employed in this invention consist of one of potassium, rubidium and cesium intercalated in either graphite or graphitized carbon black. The compounds can be represented as $C_nMe$ in which C is graphite or graphitized carbon black, Me is the alkali metal and n is an integer ranging from about 2 to about 60, more preferably from about 5 to about 50, represents the moles graphite per mole alkali metal.

EXAMPLE 1

Catalyst Preparation

The experimental carbon/potassium intercalates were prepared according to the method described in Rudorff and Schulze, Z. anorg. allg. Chem. 277, 156–171 (1954). Briefly, the method involves stirring the heated, comminuted carbon to the 300–400° C. reaction temperature employed under flowing argon. The stoichiometric amount of potassium metal is slowly added piecewise and the product is equilibrated for about one hour while continuing the stirring. The cooled product is stored under argon. Commercially obtained graphite and carbon black having a graphitic character as shown by X-rays, e.g., acetylene-derived carbon black were used as the carbon source.

The remaining graphite/alkali metal intercalates employed as catalysts are commercially available materials.

The compounds of potassium on silica were prepared by the same method used for the intercalation compounds.

EXAMPLE 2

Each $C_8K$ catalyst employed was charged to a tubular reactor under flowing argon in the form of a fixed bed, the argon was cut off and 1-butene was passed over the catalyst. The effluent product was analyzed intermittently by gas-liquid chromatography for 1-butene, trans-2-butene and cis-2-butene. The quantities of each catalyst used, reaction temperature employed, space velocities used and results obtained are presented in Tables 1a, 1b and 1c. The following abbreviations are employed:

$1-C_4^=$ means 1-butene
$t-2-C_4^=$ means trans-2-butene
$c-2-C_4^=$ means cis-2-butene
t/c mole ratio means trans/cis mole ratio The calculated space velocities are nominal values based on 0° C. and 760 mm Hg.

Table 1a

| Isomerization Of 1-Butene Over $C_8K$ At 25° C. | | | | | | |
|---|---|---|---|---|---|---|
| Sample No. | 1 | 2 | 3 | 4 | 5 | 6 |
| Time on Stream, min. | 5 | 15 | 25 | 35 | 45 | 60 |
| Flow 1-Butene cc/min | 10.6 | 10.6 | 9.4 | 10.6 | 10.6 | 10.6 |
| Calc. WHSV | 0.94 | 0.94 | 0.83 | 0.94 | 0.94 | 0.94 |
| Mole % Conversion | 45.5 | 29.5 | 18.2 | 6.4 | 1.8 | 0.2 |
| $1-C_4^=$ | 54.5 | 70.5 | 81.5 | 93.6 | 98.2 | 99.8 |
| $t-2-C_4^=$ | 8.52 | 5.38 | 3.22 | 1.07 | 0.28 | 0 |
| $c-2-C_4^=$ | 37.0 | 24.1 | 15.0 | 5.32 | 1.50 | 0.15 |

Table 1a-continued

| Isomerization Of 1-Butene Over $C_8K$ At 25° C. | | | | | | |
|---|---|---|---|---|---|---|
| Sample No. | 1 | 2 | 3 | 4 | 5 | 6 |
| Mole Ratio t/c | 0.23 | 0.22 | 0.22 | 0.20 | 0.19 | — |

Extrapolated t/c mole ratio at zero conversion is 0.20.
Catalyst weight = 0.17 g.

Table 1b

| Isomerization Of 1-Butene Over $C_8K$ At 100° C. | | | | | | | | |
|---|---|---|---|---|---|---|---|---|
| Sample No. | 1 | 2 | 3 | 4 | 5 | 6 | 7 | 8 |
| Time On Stream, min. | 5 | 25 | 45 | 60 | 75 | 90 | 105 | 120 |
| Flow 1-Butene cc/min | 9.5 | 8.7 | 10.7 | 10.7 | 9.9 | 9.1 | 18.0 | 17.7 |
| Calc. WHSV | 0.64 | 0.59 | 0.72 | 0.72 | 0.67 | 0.61 | 1.2 | 1.2 |
| Mole % Conversion | 9.9 | 7.3 | 4.0 | 3.2 | 2.8 | 2.3 | 1.3 | 1.3 |
| 1-$C_4^=$ | 90.1 | 92.7 | 96.0 | 96.8 | 97.2 | 97.6 | 98.7 | 98.7 |
| t-2-$C_4^=$ | 2.64 | 1.94 | 1.03 | 0.80 | 0.72 | 0.68 | 0.35 | 0.34 |
| c-2-$C_4^=$ | 7.24 | 5.32 | 2.95 | 2.34 | 2.04 | 1.74 | 0.98 | 0.97 |
| Mole Ratio t/c | 0.36 | 0.36 | 0.35 | 0.34 | 0.35 | 0.39 | 0.36 | 0.35 |

Extrapolated t/c mole ratio at zero conversion is 0.35.
Catalyst weight = 0.20 g.

Table 1c

| Isomerization Of 1-Butene Over $C_8K$ At 150° C. | | | | | | |
|---|---|---|---|---|---|---|
| Sample No. | 1 | 2 | 3 | 4 | 5 | 6 |
| Time On Stream, min. | 5 | 45 | 75 | 105 | 120 | 130 |
| Flow 1-Butene cc/min | 9.0 | 9.0 | 9.0 | 19.5 | 33.8 | 35.0 |
| Calc. WHSV | 0.48 | 0.48 | 0.48 | 1.05 | 1.8 | 1.9 |
| Mole % Conversion | 13.4 | 8.9 | 8.9 | 8.1 | 6.5 | 2.0 |
| 1-$C_4^=$ | 86.6 | 91.1 | 91.1 | 91.9 | 93.5 | 98.0 |
| t-2-$C_4^=$ | 5.0 | 3.0 | 3.0 | 2.7 | 2.2 | 0.6 |
| c-2-$C_4^=$ | 8.4 | 5.9 | 5.9 | 5.4 | 4.3 | 1.4 |
| Mole Ratio t/c | 0.60 | 0.51 | 0.51 | 0.50 | 0.51 | 0.43 |

Extrapolated t/c mole ratio at zero conversion is 0.48.
Catalyst weight = 0.25 g.

It is known that potassium is an active catalyst for the isomerization of butenes at 25° C. For example, it is shown in Ikefuji, Y. et al Chemistry Letters 805–806 (1975) that cis-2-butene is selectively formed from 1-butene at 25° C. giving a trans/cis mole ratio of 0.1–0.2. At higher temperatures, 90°–140° C., this selectivity is lost giving a trans/cis mole ratio of 1.

Inspection of the results presented in Tables 1a–c show that at room temperature the invention catalyst performs similarly to prior art alkali metal catalysts with respect to forming butene isomers from 1-butene with an expected trans/cis mole ratio of about 0.2. However, at reaction temperatures of 100° C. and 150° C., the invention catalyst still selectively produces cis-2-butene from 1-butene at trans/cis mole ratios that are substantially lower than about 1. Thus, at 100° C. a trans/cis mole ratio of 0.35 is shown and at 150° C. a trans/cis mole ratio of 0.48 is shown. The values given are extrapolated from the measured values to zero conversion to obtain a standard basis of comparison.

The measured results show at low to medium conversions that low trans/cis mole ratios are obtained with the invention catalyst.

EXAMPLE 3

An intercalate of graphite and potassium was prepared corresponding to $C_{36}K$ following the previously described procedure. Under flowing argon, 0.17 g of the catalyst was charged to the reactor and 1-butene was then passed over the catalyst at 25° C. at the rate of 6.5 cc/minute equivalent to 0.52 WHSV. The effluent was analyzed as described in Example 2. The results obtained are presented in Table 2.

Table 2

| Isomerization Of 1-Butene Over $C_{36}K$ At 25° C. | | | | |
|---|---|---|---|---|
| Sample No. | 1 | 2 | 3 | 4 |
| Time On Stream, min. | 5 | 15 | 25 | 35 |
| Mole % Conversion | 89.0 | 81.5 | 59.2 | 17.3 |
| 1-$C_4^=$ | 11.0 | 18.5 | 40.8 | 82.7 |
| t-2-$C_4^=$ | 21.1 | 17.7 | 11.7 | 3.0 |
| c-2-$C_4^=$ | 67.9 | 63.8 | 47.9 | 14.3 |
| Mole Ratio t/c | 0.31 | 0.28 | 0.24 | 0.21 |

Extrapolated t/c mole ratio at zero conversion is 0.15.

The results in Table 2 show that at high conversion of 1-butene to 2-butenes, a low trans/cis mole ratio is obtained. Thus, sample 1 shows at 89% conversion of 1-butene that the trans/cis mole ratio is 0.31.

EXAMPLE 4

A series of runs was made in which 1-butene was passed over the catalyst employed in the manner previously described. Several reaction temperatures were used with each catalyst in separate runs. The nature of the catalysts employed, space velocities used, reaction temperatures employed and results obtained after 5 minutes on stream are presented in Table 3.

Table 3

Isomerization Of 1-Butene Over Various Catalysts

| Run No. | Catalyst Description | Catalyst Weight g | Reaction Temp. °C | Flow 1-Butene cc/min. | Flow Calc. WHSV | Conversion | Mole % 1-C$_4$= | Mole % t-2-C$_4$= | Mole % c-2-C$_4$= | Mole Ratio t/c At 5 min. | Mole Ratio t/c At Zero Conversion | Remarks |
|---|---|---|---|---|---|---|---|---|---|---|---|---|
| 1 | C$_8$K (carbon black)[1] | 0.16 | 25 | 11.2 | 0.94 | 7.2 | 92.8 | 1.4 | 5.7 | 0.25 | 0.22 | invention catalyst |
| 2 | C$_8$K (carbon black)[1] | 0.08 | 100 | 7.7 | 1.3 | 4.5 | 95.4 | 1.3 | 3.2 | 0.41 | 0.42 | invention catalyst |
| 3 | C$_8$Rb | 0.30 | 25 | 5.6 | 0.25 | 37.8 | 62.2 | 6.2 | 31.6 | 0.20 | 0.17 | invention catalyst |
| 4 | C$_8$Rb | 0.27 | 100 | 19.6 | 0.98 | 7.6 | 92.4 | 1.7 | 5.8 | 0.29 | 0.35 | invention catalyst |
| 5 | C$_8$Cs | 0.25 | 25 | 8.8 | 0.48 | 19.9 | 80.1 | 2.9 | 17.0 | 0.17 | 0.16 | invention catalyst |
| 6 | C$_8$Cs | 0.27 | 100 | 8.8 | 0.44 | 53.1 | 46.9 | 14.0 | 39.1 | 0.36 | 0.23 | invention catalyst |
| 7 | C$_{48}$K | 0.16 | 25 | 6.5 | 0.55 | 82.2 | 17.8 | 16.2 | 66.0 | 0.25 | 0.20 | invention catalyst |
| 8 | C$_{48}$K | 0.27 | 100 | 10.0 | 0.45 | 1.4[2] | 98.6 | 0.3 | 1.1 | 0.27 | 0.48 | invention catalyst |
| 9 | graphite[3] | 0.30 | 25 | 6.5 | 0.29 | 0 | 0 | 0 | 0 | 0 | 0 | control |
| 10 | SiO$_2$ | 0.27 | 25-200 | 1 to 10 | 0.05 to 0.5 | 0 | 0 | 0 | 0 | 0 | 0 | control |
| 11 | 8 wt. % K/92 wt. % SiO$_2$ | 0.25 | 100 | 1 | 0.05 | 0.52 | 99.6 | 0.18 | 0.26 | 0.69 | 0.71[4] | control |
| 12 | 8 wt. % K/92 wt. % SiO$_2$ | 0.25 | 150 | 1 | 0.05 | 3.5 | 96.5 | 1.7 | 1.8 | 0.94 | 1.0[5] | control |

Notes:
[1]Catalyst prepared by reacting stoichiometric amounts of potassium and acetylene black (Shawinigan Co.).
[2]Low conversion believed due to deterioration of catalyst in storage or poison in 1-butene feed.
[3]Union Carbide SP-1-C, heated in nitrogen to 300° C. prior to isomerization test.
[4]Also run at 0.5 and 2 cc/min. giving t/c values of 0.68 and 0.70, respectively. No reaction at 25° C.
[5]Also run at 2, 3 and 10.5 cc/min. giving t/c values of 0.72, 1.03 and 1.00, respectively.

The results in Table 3 reveal that the invention catalysts of runs 1–8 show good selectivity to formation of cis-2-butene from 1-butene at 25° C. and at 100° C. The trans/cis molar ratio of the 2-butene is consistently low at both 25° C. and 100° C., at conversion ranging from about 1% to about 82%. Graphite alone is inactive as a catalyst at the conditions employed as run 9 shows. Silica alone is also inactive as a catalyst at the conditions used as run 10 shows. A catalyst prepared by mixing potassium with silica in the procedure used in forming the alkali metal/graphite intercalates is not very active for butene isomerization as runs 11 and 12 show. Moreover, the trans/cis ratios of the 2-butenes produced with the control catalysts is substantially higher at 100° C. and 150° C. then the values obtained at those temperatures with the invention catalysts.

We claim:

1. A method for isomerizing aliphatic 1-olefins represented by the formula

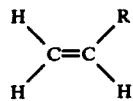

where R is selected from alkyl groups containing from 2 to about 13 carbon atoms, said method comprising contacting at a temperature in the range of about 25° C. to about 150° C. said 1-olefin with a catalyst comprising an alkali metal selected from the group consisting of potassium, rubidium, and cesium said metal intercalated in a graphite or graphitized carbon black thereby maintaining a low trans/cis ratio in isomerized product.

2. A method of claim 1 wherein reaction conditions comprise a reaction pressure in the range of about 0.5 atmospheres to about 50 atmospheres.

3. A method of claim 2 wherein the weight hourly space velocity of the 1-olefin feedstock is in the range of about 0.02 to about 20.

4. A method of claim 1 wherein the catalyst comprises about 2 to about 6 moles of graphite compound per mole of alkali metal.

5. A method of claim 4 wherein the catalyst comprises about 8 moles of graphite to 1 mole of potassium and 1-butene is converted to trans-2-butene and cis-2-butene.

6. A method of claim 4 wherein the catalyst comprises about 36 moles of graphite to 1 mole of potassium and 1-butene is converted to trans-2-butene and cis-2-butene.

7. A method of claim 4 wherein the catalyst comprises potassium and acetylene black.

8. A method of claim 1 wherein the contacting is carried out at a temperature in the range of about 100° C. to about 150° C.